United States Patent [19]

Minton et al.

[11] Patent Number: 5,008,291

[45] Date of Patent: * Apr. 16, 1991

[54] METHOD AND COMPOSITION FOR ACHIEVING CHEMOTHERAPEUTIC ACTIVITY

[75] Inventors: John P. Minton; Thomas E. Webb; Hussein M. Abou-Issa, all of Columbus, Ohio

[73] Assignee: Ohio State University Research Foundation, Columbus, Ohio

[*] Notice: The portion of the term of this patent subsequent to Apr. 23, 2008 has been disclaimed.

[21] Appl. No.: 436,046

[22] Filed: Nov. 13, 1989

Related U.S. Application Data

[63] Continuation-in-part of Ser. No. 89,568, Aug. 26, 1987, abandoned.

[51] Int. Cl.$^5$ ............................................. A61K 31/185
[52] U.S. Cl. ..................................... 514/578; 514/613
[58] Field of Search ................................. 514/578, 613

[56] References Cited

PUBLICATIONS

Oredipe et al., Cancer Letters, 1987; 38:95–99.
Walaszek et al., Cancer Letters, 1986; 33:25–32.
Dwivedi et al., J. Environ. Pathol. Toxicol. and Oncol., JEPTO, 1989, 9:3/253–260.
Walaszek et al., Carcinogenesis, 1986; 7:1463–1466.
Walaszek et al., Carcinogenesis, 1984; 5:767–772.
Walaszek et al., IRCS Medical Science, 1986; 14:677–678.
Dwivedi et al., The FASEB Journal, 1987; 1:303–307.
Moon et al., *The Retinoids*, vol. 2, New York:Academic Press, 1984; 327–371.
Thompson et al., J. Natl. Cancer Inst., 1986; 77:595–598.
Moon et al., Nature, 1977; 267:620–621.
Abou-Issa et al., Biochem. Biophys. Res. Comm., 1986; 135:116–123.
Moon et al., Cancer Res., 1979; 39:1339–1349.
Rustin et al., Brit. J. Cancer, 1985; 51:443–445.
Welsch et al., *Diet, Nutrition, and Cancer*, 1986; (B. S. Reddy and L. A. Cohen eds.) CRS Press, Boca Raton, FL pp. 1–21 (1986).
Schamberger, Diet, Nutrition, and Cancer, (B. S. Reddy and L. A. Cohen eds.) CRS Press, Boca Raton, Fl., pp. 43–62 1986.
Moon et al., Cancer Res., 1976; 36:2626.
Abou-Issa et al., Proc. Natl. ACad. Sci., (U.S.) 1988; 85;4181–4184.

Primary Examiner—Mary C. Lee
Assistant Examiner—Peter James Davis
Attorney, Agent, or Firm—Emch, Schaffer, Schaub & Porcello Co.

[57] ABSTRACT

The present invention describes a dietary supplement for achieving a very high degree of chemotherapeutic activity through the synergistic combination of a low suboptimal dose of a D-glucarolactone-based dietary anticarcinogen (calcium glucarate) with a low suboptimal dose of retinoid-based anticarcinogen (4-hydroxyphenyl retinamide).

7 Claims, 5 Drawing Sheets

EFFECT OF DIETS ON MEAN NUMBER OF TUMORS / RAT

✶ CONTROLS (CHOWDIET)
△ 1.5 % HPR
☐ 0.75 mmol/kg HPR + 1 % CGT
▨ 0.75 mmol/kg HPR + 2 % CGT

EFFECT OF DIETS ON % RATS WITH TUMORS

✳ CONTROLS (CHOWDIET)

○ 1 % CGT

⦿ 2 % CGT

☐ 0.75 mmol/kg HPR + 1 % CGT

▨ 0.75 mmol/kg HPR + 2 % CGT

△ 1.5 mmol/kg HPR

▲ 0.75 mmol/kg HPR

EFFECT OF DIETS ON MEAN WEIGHTS OF RATS (gm)

* CONTROLS (CHOWDIET)
○ 1.0 % CGT
⊙ 2.0 % CGT
□ 0.75 mmol/kg HPR + 1 % CGT
▨ 0.75 mmol/kg HPR + 2 % CGT
△ 1.5 % HPR

METHOD AND COMPOSITION FOR ACHIEVING CHEMOTHERAPEUTIC ACTIVITY

The present invention is a continuation-in-part of patent application Ser. No. 089,568, filed Aug. 26, 1987, now abandoned.

This invention relates generally to a dietary supplement for achieving a very high degree of anticarcinogenic or chemopreventive activity and particularly relates to a combination of a low suboptimal doses of a D-glucarolactone-based dietary anticarcinogen with a low suboptimal doses of a retinoid-based anticarcinogen.

BACKGROUND OF THE INVENTION

Various glucarolactone-based compounds, including calcium glucarate (CGT), micro-encapsulated D-glucaro-1,4-lactone, potassium hydrogen glucarate and 2,4-di-O-acetyl-D-glucaro-1,4-lactone, are known to be effective as inhibitors of beta-glucuronidase in cells, blood, urine and in the intestine and liver. By inhibiting beta-glucuronidase, less detoxified (that is glucuronidated) toxins are hydrolysed and therefore more toxins are excreted. As a result, such glucarolactone-based compounds are useful in the treatment and prevention of various types of cancer.

Recently glucarate in the sustained release dietary form of calcium glucarate, was found to be a potent chemopreventative agent in the rodent system as having preventative activity against chemical carcinogenesis (both initiation and promotion phases) in the liver, Oredipe, O. A., et al., Effects of calcium glucarate on the promotion of diethylnitrosamine-initiated altered hepatic foci in rats in Cancer Letters 38: 95-99 (1987); lung, Walaszek, Z., et al., Dietary glucarate-mediated reduction of sensitivity of murine strains to chemical carcinogenesis in Cancer Letters 33: 25-32 (1986); skin, Dwivedi, C., et al., Modulation of chemically initiated and promoted skin tumorigenesis in CD-1 mice by dietary glucarate in *J. Environ. Pathol. Toxicol. and Oncol.*, in press; and mammary gland, Walaszek, Z., et al., Dietary glucarate as anti-promoter of 7,12-dimethylbenz(a)anthracene-induced mammary tumorigenesis in Carcinogenesis, 7: 1463-1466 (1986). See, also for example, Walaszek, Z. et al. Inhibition of 7,12-dimethylbenzanthracene-induced rat mammary tumorigenesis by 2,5-di-0-acetyl-D-glucaro-1,4:6,3-dilactone, an in-vivo beta-glucuronidase inhibitor. Carcinogenesis 5: 767-772, (1984); and, Walaszek, Z., et al., Inhibition of N-methyl-N-nitrosourea-induced mammary tumorigenesis in the rat by a beta-glucuronidase inhibitor. IRCS Medical Science 14: 677-678, (1986).

In Walaszek et al., Carcinogenesis 7, supra, preliminary evidence was obtained that glucarate also inhibits and indeed causes regression of DMBA-induced rat mammary tumors. Glucarate is a normal body constituent, as it is the end product of glucuronic acid metabolism which is excreted in the urine. However, glucarate is present in blood and tissues at very low levels. Glucarate is non-toxic in dosages up to 10% in the diet as calcium glucarate and is effective at dietary levels of 4% (128 mmol/kg diet). In the systems studied to date it has been indicated that the active component is glucarate. Glucarate can undergo equilibrium formation of D-glucaro-1,4-lactone. Through inhibition of beta-glucuronidase, the lactone effects net formation of glucuronide conjugates of certain carcinogens or promoting agents in the phase II detoxification reactions, Dwivedi, C., et al., Net glucuronidation in different rat strains: Importance of microsomal beta-glucuronidase. The FASEB Journal, 1: 303-307 (1987).

Retinoid-based compounds including retinylacetate, retinylmethyl ether, 13-cis-retinoic acid and N-(4-hydroxyphenyl) retinamide (HPR), have similarly been investigated for their anticarcinogenic activity. These retinoids, both natural and synthetic, have been under intensive investigation as both cancer chemopreventative agents and anti-cancer (chemotherapeutic) agents, Moon, R. C., et al., Retinoids and cancer. In Sporn, M. B., Roberts, A. B., Goodman, D. S. eds., The retinoids, Vol 2. New York: Academic Press, 327-371 (1984) and Thompson, H. J., et al., Comparative review of the efficacy of a polyamine antimetabolite retinoids and selenium. J. Natl. Cancer Inst. 77: 595-598 (1986). Retinoids have been shown to be very effective at or near toxic levels in several experimental animal systems including MNU, Moon, R. C., et al., Retinylacetate inhibits mammary carcinogenesis induced by N-methyl-N-nitrosourea, Nature 267: 620-621 (1977); and the 7,12-dimethylbenz(a)anthracene (DMBA)-induced rat mammary tumor system, Abou-Issa, H., et al., Anticarcinogenic effect of retinoids on 7,12-dimethylbenz(a)anthracene-induced mammary tumor induction, and its relationship to cyclic AMP-dependent protein kinase, Biochem. Biophys. Res. Commun., 135: 116-123 (1986). Many of the toxicity problems were minimized in protocols associated with mammary carcinogenesis with the introduction of the synthetic retinoid N-(4-hydroxyphenyl)retinamide which displays trophism for the mammary gland, Moon, R. C., et al., N-4-Hydroxyphenyl retinamide, a new retinoid for preventing breast cancer in the rat, Cancer Res. 39: 1339-1349 (1979). This compound is currently being tested clinically in combination with the anti-estrogen Tamoxifen ®, in the prevention of breast cancer in women at risk, Rustin, G. J. S., et al., The potential use of retinoids in oncology (Meeting Report). Brit. J. Cancer 51: 443-445 (1985). [See also, Abou-Issa, H., et al., Anti-carcinogenic effect of retinoids on 7,12-dimethylbenz(a)anthracene-induced mammary tumor formation and its relation to cyclic AMP-dependent kinase Biochem. Biophys. Res. Commun. 135: 116-123, (1986); Welsch, C. W., et al., Retinoids and Mammary gland tumorigenesis in *Diet, Nutrition and Cancer* (B. S. Reddy and L. A. Cohen eds.) CRS Press Boca Raton, FL. pp 1-21, (1986); Schamberger, R. J. Chemoprevention of cancer in *Diet, Nutrition and Cancer*. (B. S. Reddy and L. A. Cohen eds.) CRC Press, pp. 43-62, (1986); and, Moon, R. C., Inhibition of 7,12-dimethylbenzanthracene-induced mammary carcinogenesis by retinyl acetate. Cancer Res. 36: 2626, (1976).]

These studies confirmed the activity of relatively high doses of retinoids against the chemical induction of mammary carcinogenesis in the rat. Similarly, high dosages were tested against the chemical carcinogen-mediated induction of tumors in the mammary gland, lung, skin, intestine and liver. Further, retinoids have been shown to protect skin, nasopharnyx, lower respiratory tract, urinary bladder and colon against carcinogens. In addition, these retinoic acid analogs (Vitamin A active compounds) have been tested in combination with the micronutrient selenium.

One problem associated with the use of retinoid-based compounds is that relatively high doses of the retinoids must be administered in order to achieve the desired anticarcinogen effect. Such high doses of retinoids often results in cummulative toxicity, with the excess retinoids being deposited in the liver.

Because relatively high levels of around 4% of dietary calcium glucarate are required for maximum effectiveness, and because of potential retinoid toxicity and the desire to increase the therapeutic index, the combination of the retinoid and glucarate was disclosed in the parent patent application Ser. No. 089,568. Surprisingly, when low ineffective dosages (approximately one-half the effective dose or less) of HPR and CGT were combined in the diet, they interacted synergistically to inhibit carcinogenesis to the extent of high effective dosages of either agent alone. The results of this patent application were later reported in Abou-Issa, H. M., et al., Putative metabolites derived from dietary combinations of calcium glucarate and N-(4-hydroxyphenyl)retinamide act synergistically to inhibit the induction of rat mammary tumors by 7,12-dimethylbenz-(a)anthracene. Proc. Natl. Acad. Sci. (U.S.) 85: 4181–4184 (1988). This combination has now been further evaluated as a chemotherapeutic agent on established DMBA-induced rat mammary tumors. The results disclosed herein indicate that the combination of the retinoid and the glucarate also interact synergistically to inhibit rat mammary tumor growth.

There has been no suggestion in the art that a combination of glucarolactone-based compounds and retinoid-based compounds would be especially useful as anticarcinogens; that is, that the combination of these compounds would represent an alternative for use in the prevention of cancer or for use in the therapeutic treatment of cancer.

It has now been found that the use of a combination of glucarolactone-based compounds and retinoid-based compounds or their pharmaceutically-acceptable salts and esters, compounds which are known to be safely administered to humans and animals, significantly inhibit tumor growth and to shrink tumors.

It is therefore an object of the present invention to provide a safe and effective dietary supplement and method for inhibiting tumor growth and for reducing the incidence of cancer in certain high risk populations.

Other objects and advantages of the invention will be apparent from the following detailed description of the invention.

SUMMARY OF THE INVENTION

The present invention describes a protocol for achieving a very high degree of chemotherapeutic activity through the combination of a low suboptimal dose of a D-glucarolactone-based dietary anticarcinogen (namely, calcium glucarate) with a low suboptimal dose of retinoid-based anticarcinogen (namely, 4-hydroxyphenyl retinamide). Since synergism is obtained by this combination, these two anticarcinogens can be employed at dosages far below toxic levels and at dosages that are practical as a chemotherapeutic agent.

DESCRIPTION OF INVENTION

Figure 1:
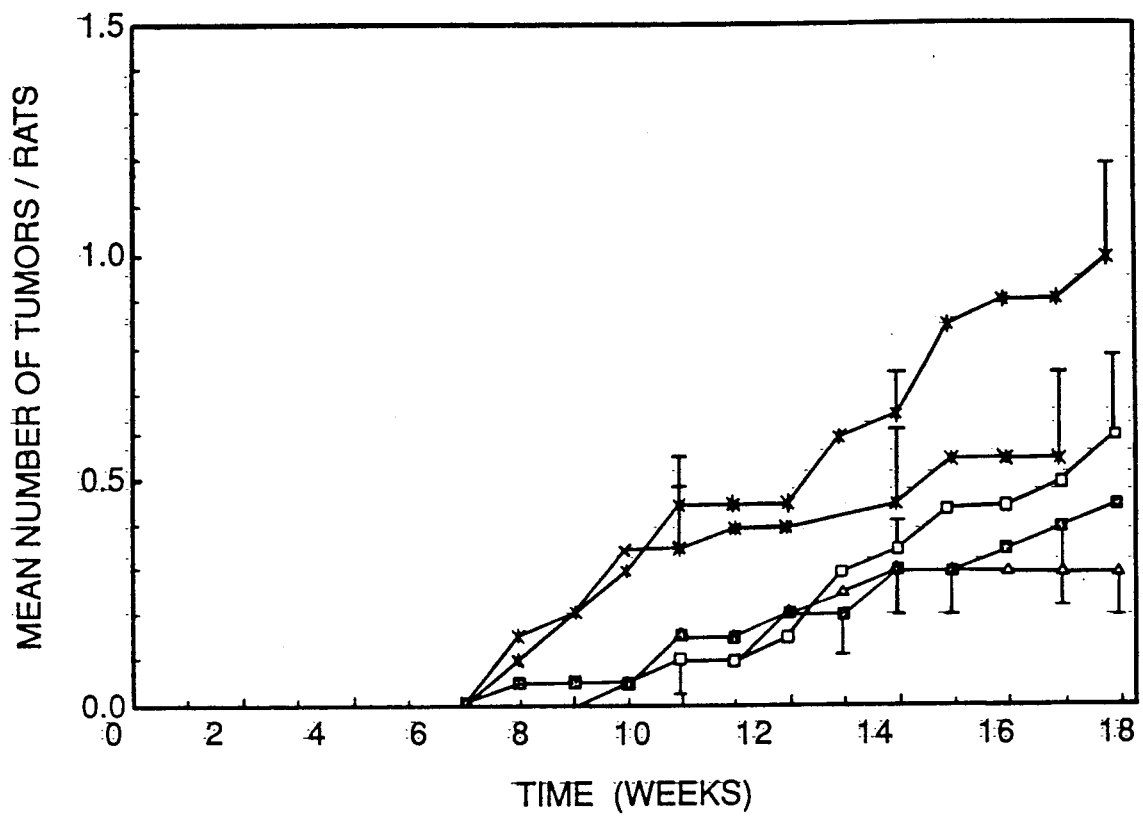
FIG. 1 is a graph showing the effect of diets on the mean number of tumors per rat: *control (chow diet); Δ 1.5% HPR; □ 0.75 mmol/kg HPR and 1% CGT; and, 0.75 mmol/kg HPR and 2% CGT.

The present invention relates to a method for achieving a very high degree of chemotherapeutic activity comprising the administration of a safe and effective amount of a compound comprising a combination of a D-glucarolactone-based dietary anticarcinogen with a retinoid-based anticarcinogen and pharmaceutically-acceptable salts and esters thereof to a subject either in a high risk group for cancer or to a subject who has cancer.

The treatment regimens encompassed by the present invention employ a safe and effective amount of a pharmaceutically-acceptable composition comprising a combination of a glucaro-lactone-based and a retinoid-based compound. These compounds are administered to prevent the occurrence of cancer and to inhibit the growth of cancer tumor cells in humans and animals. Various glucarolactone-based compounds utilized herein are conveniently abbreviated "glucarolactone" or "GL"; "calcium glucarate" or "CGT"; various retinoid-based compounds utilized herein are conveniently abbreviated "retinoids" or "HPR". The phrase "safe and effective amount of glucarolactone/retinoid compound" herein, means sufficient glucarolactone/retinoid compound to desirably affect and inhibit the induction or growth of tumor cells, at a reasonable benefit/risk ratio attendant with any medical treatment. Within the scope of sound medical judgment, the required dosage of the glucarolactone/retinoid compound will vary with the severity of the condition being treated, the duration of the treatment, the nature of adjunct treatment, the age and physical condition of the patient, the specific glucarolactone and retinoid compounds employed, and like considerations discussed more fully hereafter.

"Pharmaceutically acceptable", as used herein, means that the glucarolactone/retinoid compound and other ingredients used in the compositions employed herein are suitable for use in contact with the tissues of humans and lower animals without undue toxicity, irritation, allergic response, and the like, commensurate with a reasonable benefit/risk ratio.

The term "administration" of the glucarolactone/retinoid compounds and compositions, as used herein includes intragastric and oral administration thereof.

The term "comprising", as used herein, means that various other compatible drugs and medicaments, as well as inert ingredients, can be conjointly employed in the therapeutic methods of this invention, as long as the critical glucarolactone/retinoid compounds are used in the manner disclosed. The term "comprising" thus encompasses and includes the more restrictive terms "consisting of" and "consisting essentially of".

By "compatible", herein, it is meant that the components of the composition used in the practice of this invention are capable of being comingled without interacting in a manner which would substantially decrease the efficacy of the glucarolactone/retinoid compositions under ordinary use situations.

The novel compositions of the invention are useful for the treatment of various cancers, such as for example, lung, colon and mammary cancers. The novel compositions may be used alone or in combination with other therapeutic agents active for these purposes. As used herein, the term "inhibition" comprehends arresting or retarding the growth of the malignancy or other manifestation of a disease, as compared with the course of the disease in the absence of treatment.

The novel compositions of the present invention are also useful to prevent the occurence of cancer in high risk populations. The compositions may be used alone or in combination with other chemopreventative agents active for these purposes. As used herein, the term "prevention" comprehends reducing the incidence of tumors in a patient or a population exposed to cancer causing agents such as cigarette smoking, or environmental toxins, as compared with the course of potential development of this disease in the absence of treatment. It also comprehends reducing endogenously produced cancer-causing agents including steroid hormones.

The mechanism of action of retinoid-based compounds such as retinylacetate, retinylmethyl ether, 13-cis-retinoic acid, and N-(4-hydroxyphenyl)retinamide (HPR) are believed to act by inducing differentiation. One of the main biochemical effects of the retinoid-based compound is to elevate the level of cellular cAMP (cyclic AMP) and of histone kinases.

Similarly, the glucarolactone-based compounds such as calcium glucarate, potassium hydrogen glucarate, micro-encapsulated D-glucaro-1,4-lactone, 2,4-di-O-acetyl-D-glucaro-1,4-lactone, when fed slowly release D-glucaro-1,4-lactone (GL), a potent inhibitor of beta-glucuronidase in the cells, blood and urine and in the intestine. Since beta-glucuronidase is inhibited, less detoxified (i.e., glucuronidated) toxins are hydrolyzed and therefore more toxins are excreted. Thus, the inhibition of beta-glucuronidase promotes clearance/excretion of detoxified (glucuronidated) compounds from the body. Not only carcinogens but other toxins, steroid hormones and other substances which undergo glucuronidation may be affected.

The above-mentioned compounds are used as dietary sources of GL since they are more effective by virtue of the fact they are sustained (slow)-release forms, GL itself being too rapidly absorbed and cleared from the body. Thus, the glucarolactone-class of inhibitors may be used to reduce the inappropriate level of any compound in the body which is subject to glucuronidation before excretion. Besides the glucarates, micro-encapsulated GL and the di-O-acetyl derivative of GL, dietary substances which may yield GL and which might be as useful as CGT include D-glucuronic acid, D-galacturic acid, L-iduric acid or derivatives or analogs thereof.

Although CGT in one embodiment of the invention is combined with retinoids it is also possible that CGT may be effectively combined with other micronutrients or even lower doses of CGT and retinoid may be combined with additional anticarcinogens. For example, calcium appears to be an anticarcinogen for colon cancer by ameliorating the toxic effects of bile acids so that the calcium glucarate/retinoid combination may be considered to be a combination of three anticarcinogens, though the protective effect of these low dosages of calcium are minimal.

A particularly interesting combination might be CGT/retinoid/ascorbic acid, since Vitamin C is protective against colon cancer. Because of activity against carcinogens attacking most major organs, whereas other anticarcinogens are more organ-specific, the glucarolactone-based/retinoid-based anticarcinogens can serve as a common component in combinations with other known anticarcinogens.

A combination of low non-toxic doses of dietary retinoid (HPR) and dietary calcium glucarate inhibited the incidence of dimethyl benz(a)anthracene-induced rat mammary tumors to a greater extent than the same doses of either agent alone. This combination was also able to reduce the number of palpable tumors by one-half (50%) as compared to rats that received the control diet, or identical doses of either agent alone. These results, which are relevant to breast cancer, may also apply to chemoprevention of cancer at other sites, including higher doses of CGT which have been shown to be effective against lung, colon and mammary carcinogenesis while retinoids are known to be effective against at least mammary and colon carcinogenesis.

A combination of suboptimal doses of retinoid and glucarolactone-based compounds is effective as an anticarcinogen. Furthermore, by reducing the dosage of the anti-cancer agents, both toxicity and impractical dosage requirements are circumvented.

EXAMPLE I

The following example demonstrates the heretofore unsuspected ability of the composition of the present invention to desirably inhibit the formation of tumors. The effect of CGT, HPR and CGT/HPR on 7,12-dimethylbenz(a)anthracene(DMBA)-induced mammary tumor formation in female Sprague Dawley rats was determined using the following protocol: Female rats maintained on one of 8 diets received 75 mg/kg of 7,12-dimethylbenz(a)anthracene in mineral oil by mouth. They were maintained on the diets for approximately 4 mos., and were examined (palpated) for mammary tumors weekly. The diets were (i) rat chow; (ii) chow and 1% CGT; (iii) chow and 2% CGT; (iv) chow and 4% CGT; (v) chow and 0.75 mmol/kg HPR; (vi) chow and 1.5 mmol/kg HPR; (vii) chow and 1% CGT and 0.75 mmol/kg HPR; and (viii) chow and 2% CGT and 0.75 mmol/kg HPR. Note: mmol/kg means mmol/kg diet; 1% CGT means 1 gm/100 gm of chow. In these experiments the CGT powder was mixed into the powdered chow diet. The retinoid (HPR) was first dissolved in 25 ml of a vehicle consisting of ethanol-tricaprylin-6% α-tocopherol, then thoroughly mixed with powdered rat chow. The results obtained, expressed in tumor incidence, total number of tumors, and tumors per rat, are summarized in the following Table I:

TABLE I

Effect of CGT, HPR and CGT & HPR on 7,12-Dimethylbenz(a)anthracene-induced Mammary Tumor formation in Female Sprague Dawley Rats

| Dietary Anti-carcinogen | No. of Rats | Rats with Tumors | Tumor Incidence | Total No. Tumors | Tumors Per Rat |
|---|---|---|---|---|---|
| None (control) | 20 | 14 | 70 | 22 | 1.1 |
| 1% CGT | 20 | 11 | 55 | 20 | 1.0 |
| 2% CGT | 20 | 11 | 55 | 20 | 1.0 |
| 4% CGT | 20 | 7 | 35 | 10 | 0.5 |
| 0.75 mmol/kg HPR | 20 | 12 | 60 | 20 | 1.0 |
| 1.5 mmol/kg HPR | 20 | 6 | 30 | 7 | 0.35 |
| 0.75 mmol/kg HPR & 1% CGT | 20 | 9 | 45 | 12 | 0.6 |
| 0.75 mmol/kg HPR & 2% CGT | 20 | 7 | 35 | 9 | 0.45 |

% CGT = gm % of calcium glucarate added to chow diet. mmol/kg HPR = moles of 4-hydroxy phenylretinamine added to chow diet per kg diet.
Protocol: 50d old female S.D. rats received a single dose 75 mg/kg of DMBA. Feeding of CGT, HPR or both was initiated 2 weeks before treatment with DMBA, then continued throughout the experiment.

When tested alone the higher doses of CGT (4%) and HPR (1.5 mmol) markedly inhibited tumorigenesis i.e., tumor incidence by 50-60% and tumors/rat by 50-65%. At lower doses the effect was minimal i.e., 1.0% CGT inhibited tumor incidence only 20% and tumors/rat by 9% while 0.75 mmol/kg HPR inhibited tumor incidence only 15% and tumors/rat by 9%. In contrast, when tested in combination, 1% CGT and 0.75 mmol/kg HPR inhibited tumor incidence by 36% and tumors/rat by 45%. Similarly 2% CGT and 0.75 mmol/kg HPR inhibited tumor incidence by 50% and tumors/rat by 60%.

Figure 2:
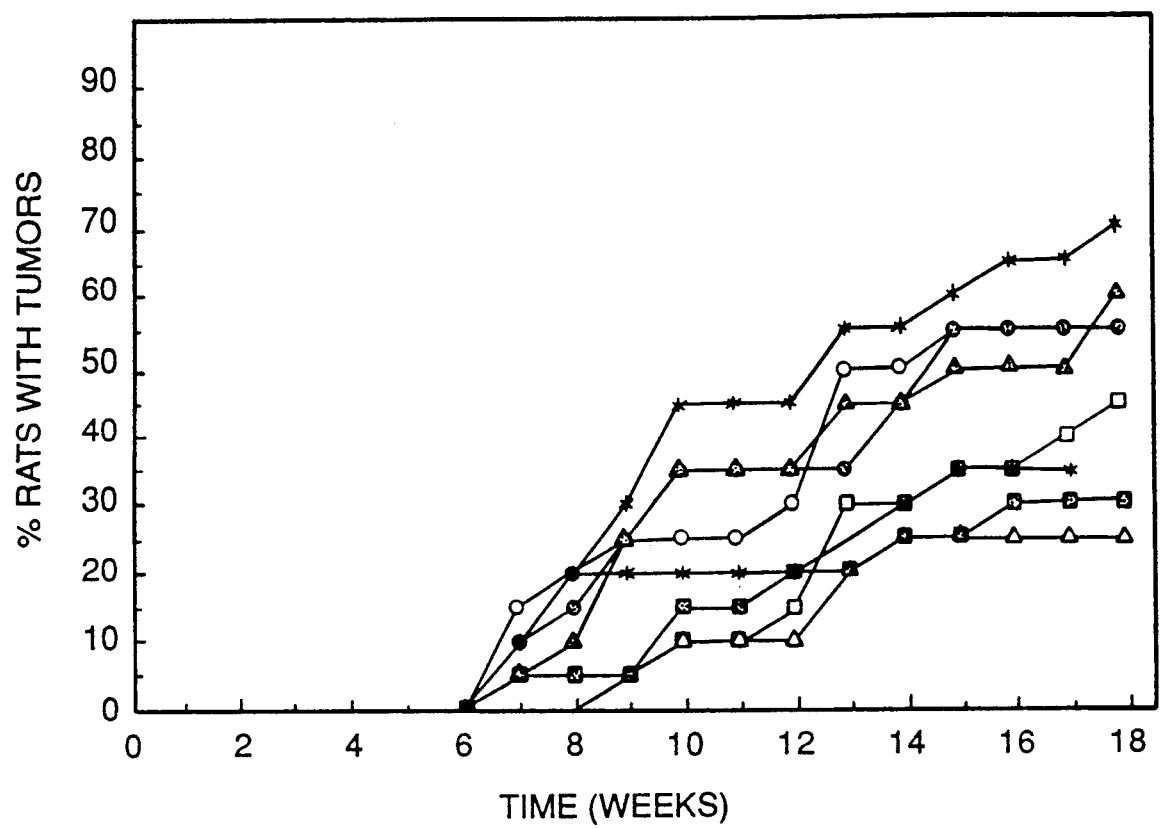
FIG. 2 is a graph showing the effect of diets on the percentage of rats with tumors: *control (chow diet); 1% CGT; 2% CGT; □ 0.75 mmol/kg HPR and 1% CGT; 0.75 mmol/kg HPR and 2% CGT; Δ 1.5 mmol/kg HPR; and 0.75 mmol/kg HPR.

The effect of the diets on the mean number of tumors per rat is shown in FIG. 1, while FIG. 2 shows the effect of the diets on the percent of rats with tumors.

Glucarolactone-based inhibitors acts to inhibit the growth of hormone-dependent tumors by lowering hormone levels. It has previously been shown in Walaszek, Z., et al., Carcinogenesis 7: 1463-1466 (1986), that dietary calcium glucarate (CGT) inhibits the promotion phase of 7,12-dimethylbenz(a)anthracene-induced mammary tumorigenesis. The female rats were put on the CGT diet two weeks after treatment with carcinogen. By 28 weeks tumor induction in the rats on the 4% CGT diet was only 30% of that in the controls, indicating CGT markedly inhibits the promotion phase in this model. Rats on the CGT-supplemented diet ate quantities of food and had weight gain identical to those on the normal chow diet. The anti-promotional effect of CGT was shown to be probably due to the reduction in the steady-state level of sex hormones. Further, and of relevance to this invention, some tumors on the chow diet supplemented with CGT underwent regression. The overall tumor incidence represents those which escape the anti-promotional effects of CGT and the equilibrium between growth and regression.

Figure 3:
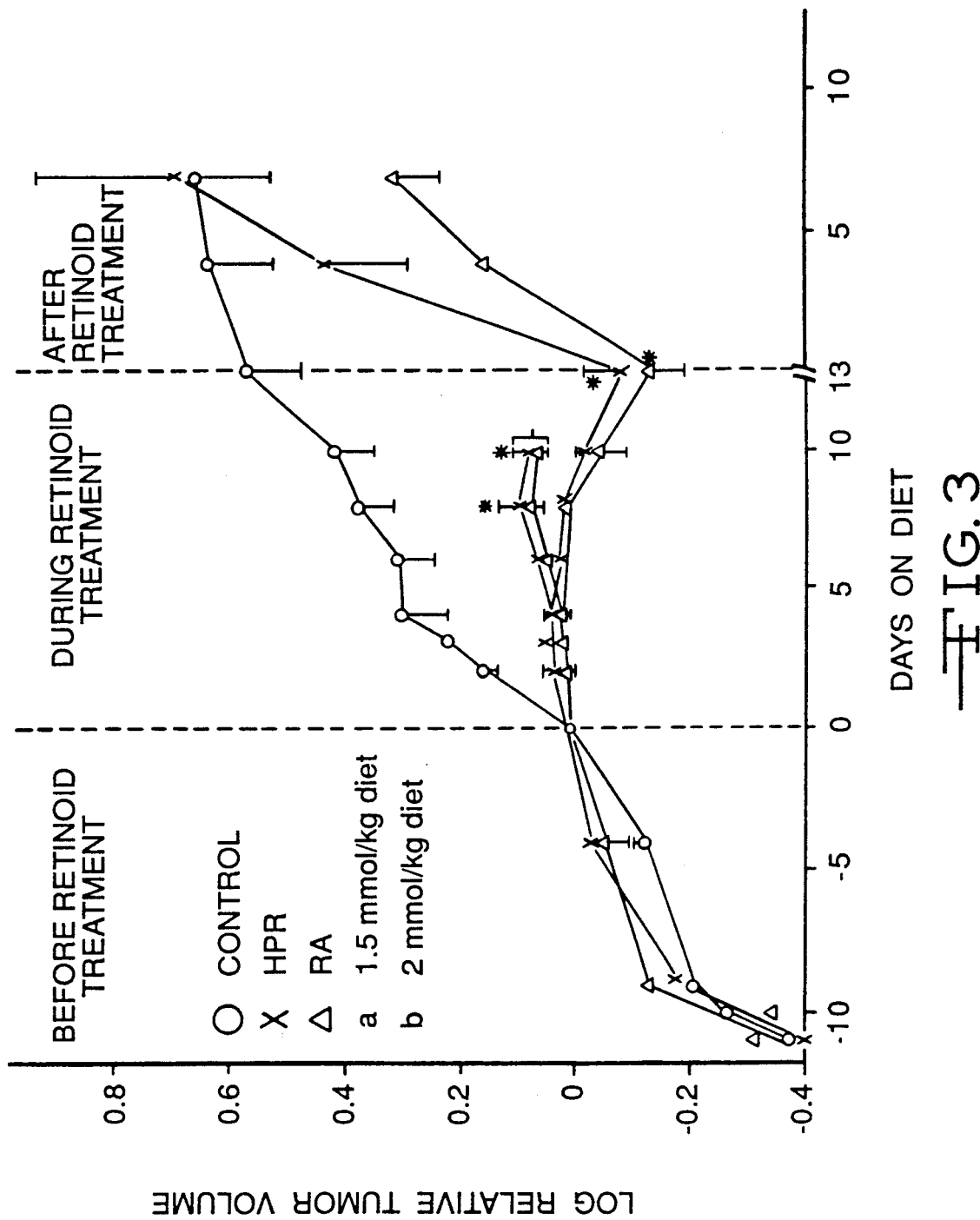
FIG. 3 is a graph showing the effects of retinoids on inhibiting growth of established cancer, before retinoid treatment, during retinoid treatment and after retinoid withdrawal: control; X HPR; Δ RA; (a) 1.5 mmol/kg diet, (b) 2 mmol/kg diet.

Similarly, retinoids, as shown in FIG. 3, inhibit growth of established cancer. The administration of 1.0 mmol/kg diet of HPR daily to female Sprague Dawley rats with already established DMBA-induced mammary tumors resulted in 80-90% inhibition of tumor growth within 10 days. Similarly, when given to $CD_8F_1$ mice with established mammary tumors this retinoid resulted in 50% inhibition of tumor growth. When higher doses (2 mmol/kg diet) of HPR were used, growth arrest was followed within 5 to 10 days by 30% regression of the DMBA-induced mammary tumors. Also, HPR (0.1 uM) inhibited the in vivo growth of the human breast cancer cell line (MCF-7) to 50% of the control within 7 days. These results suggest that retinoids have anti-tumor effects besides their cancer chemopreventive effects.

Figure 4:
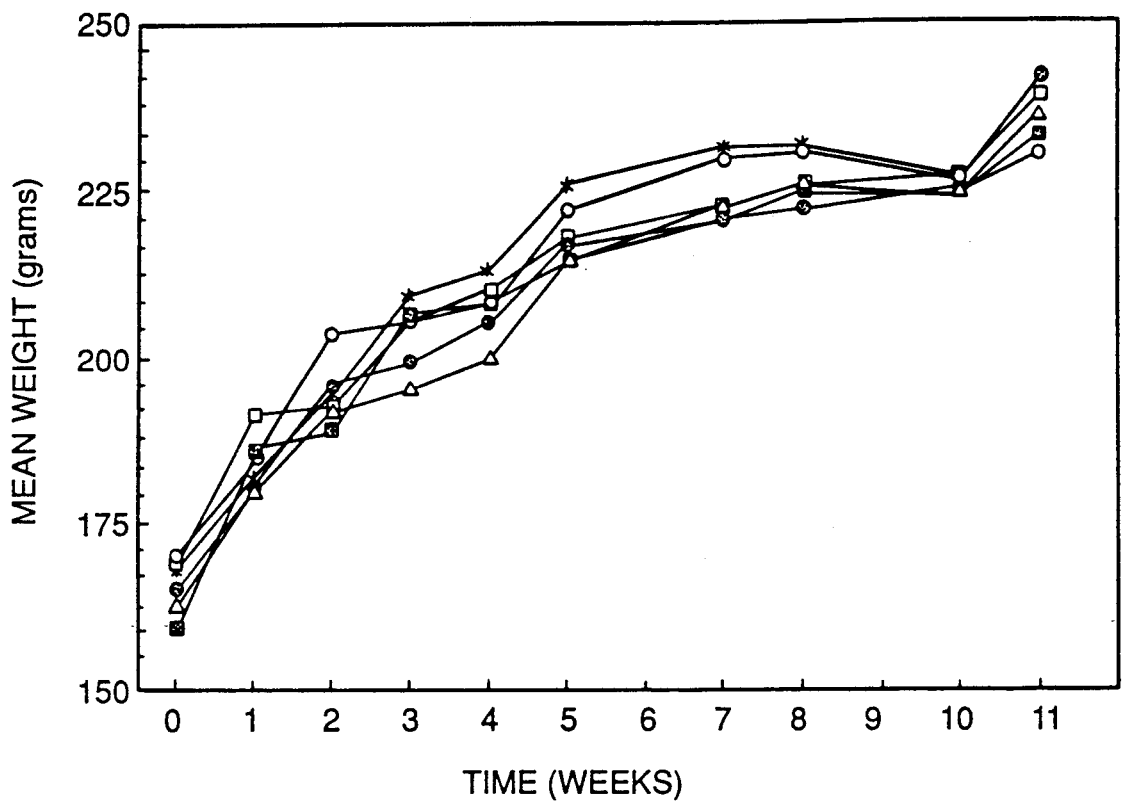
FIG. 4 is a graph showing the effect of diets on the mean weight of rats: *control (chow diet); 1.0% CGT; 2.0% CGT; □ 0.75 mmol/kg HPR and 1% CGT; 0.75 mmol/kg HPR and 2% CGT; and Δ 1.5% HPR.

As shown in FIG. 4 prolonged feeding of diets containing CGT and HPR did not affect weight gain of rats. This is important since toxicity as evidenced by marked weight loss may also influence carcinogenesis and tumorigenesis.

The effect glucarolactone (GL) alone or in combination with HPR on the growth of MCF-7 cells is shown in Table II below. The cells were plated at the density of 3775 cc per well in six well plates and treated after one day with GL-HPR- or GL and HPR-containing media for 5 days. The values shown are the mean +/− ISE for three experiments counted in triplicates. The numbers in parenthesis indicate the number of free floating (mostly non viable) cells in the media. As can be seen, the GL/HPR-containing media had only one-third the viable cells as the control medium. The GL $(10^{-4}M)$/HPR$(5 \times 10^{-8}M)$-containing medium had nearly one-third the viable cells as the GL $(10^{-4}M)$ medium alone and had nearly one-half the viable cells as the HPR$(5 \times 10^{-8}M)$ medium alone. These experiments indicate that the combination of GL and HPR is capable of inhibiting tumor cell growth and that such combination is more effective than either the GL- or HPR-containing media alone in inhibiting tumor cell growth.

TABLE II

| Treatment | No. of viable cells | % of control |
|---|---|---|
| 0.1% Ethanal | 60400 ± 2147 (6440) | 100 ± 4 (11) |
| GL $(10^{-4}M)$ | 49480 + 3160 (3440) | 82 + 5 (6) |
| GL $(10^{-3}M)$ | 32560 ± 1800 (4560) | 54 ± 3 (7) |
| HPR $(5 \times 10^{-8}M)$ | 33680 ± 2627 (4160) | 56 ± 4 (7) |
| GL $(10^{-4}M)$ + HPR $(5 \times 10^{-8}M)$ | 18160 ± 1568 (5280) | 30 ± (9) |
| GL $(10^{-3}M)$ + HPR $(5 \times 10^{-8}M)$ | 22680 ± 1863 (2960) | 37 ± 3 (5) |

EXAMPLE II

The following example demonstrates the heretofore unsuspected ability of the composition of the present invention to not only desirably inhibit tumor growth but also shrink tumors. Rat mammary tumors were induced by treating one hundred 50 day old female Sprague Dawley rats (Harlan Industries, Indianapolis, Ind.) by gavage with a single dose of 15 mg of 7,12-dimethylbenz(a)anthracene (Sigma Chemical Co., St. Louis, Mo.) in 1.0 ml of sesame oil, Abou-Issa et al., Proc. Natl. Acad. Sci. U.S.A., supra. The rats were maintained on a chow diet ad libitum until the tumors had formed in 70% of the rats and had reached a size of approximately 2.0 cm in diameter; 4 months later at which time they were randomized into six groups of 10 rats each. Tumor sizes were measured in all the rats just before placing them on the following experimental diets (Groups I–VI): (I) rat chow (RMH 3200, Pro Lab, Syracuse, N.Y.); (II) rat chow with HPR (1.5 mmol/kg); (III) rat chow with 4% CGT 3.5 $H_2O$ Gallard Schlesinger, Carle Place, N.Y.) (128 mmol/kg of diet); (IV) rat chow with HPR (0.75 mmol/kg); (V) rat chow with 2% CGT (64 mmol/kg); (VI) rat chow with the combination 2% CGT (64 mmol/kg) and HPR (0.75 mmol/kg). The CGT was added as a powder directly to the diet, while the HPR was first dissolved in 25 ml of ethanol/tricaprylin 1:4 (vol/vol) plus 6% (wt/vol) α-tocopherol, as previously described in Abou-Issa et al., Proc. Natl. Acad. Sci. U.S.A., supra. The latter vehicle was added to the diet of all six groups. The additives were blended into the diet with a mechanical mixer.

All the tumors that developed within the time frame of this example are histologically adenocarcinomas. This finding has been previously reported by Huggins et al., Mammary cancer induced by a single feeding of polynuclear hydrocarbons, and its suppression, Nature, 185:204–207 (1961), in this animal model under the same conditions, and has been confirmed in several indentical experiments. At later time periods beyond the time frame of this example fibroadenomas usually develop, Welsch et al., In "Cellular and Molecular Biology of Mammary Cancer", (W. Kidwell, G. Heppner and E. Anderson, eds.) Plenum Press, N.Y. 1987, pp 163–179. Tumor measurements were began at the time the rats were placed on the experimental diets and were continued twice weekly throughout the duration of the experiment. Two axes were measured - the longest axis (L) and the axis at right angles to the longest (W), using a vernier caliper. Tumor volume was calculated from the formula 4/3 pi $r^3$, where r is half the mean of the two diameters in accordance with Steel, Growth kinetics of tumors, Oxford Univ. Press, London, pp 5–25, 1977.

Tumor regression is indicated by at least 20% reduction in tumor size and each tumor is compared to its initial size on day zero. Weights of the rats on the control and experimental diets were recorded weekly.

Estrogen and progesterone receptors were measured in the OSU Hormone Receptor Laboratory by the multipoint dextran-coated charcoal method as previously described in Schuller et al., Estrogen and progesterone receptors in head and neck cancer, Arch. Otolaryng. 110:725–727 (1984). The data of specific binding were analyzed by Scatchard, The Attraction of proteins for small molecules and ions, Ann. N.Y. Acad. Sci. 51:660–672 (1949), plots to determine the equilibrium dissociation constant ($K_d$) and binding capacity expressed as femtomoles of estradiol or progesterone (R-5020) specifically bound per mg of cytosol protein for estrogen and progesterone receptors respectively. Cytosol protein concentrations were determined by the procedure of Lowry et al., Protein measurement with the folin phenol reagent, J. Biol. Chem. 193:265–275 (1951).

Figure 5:
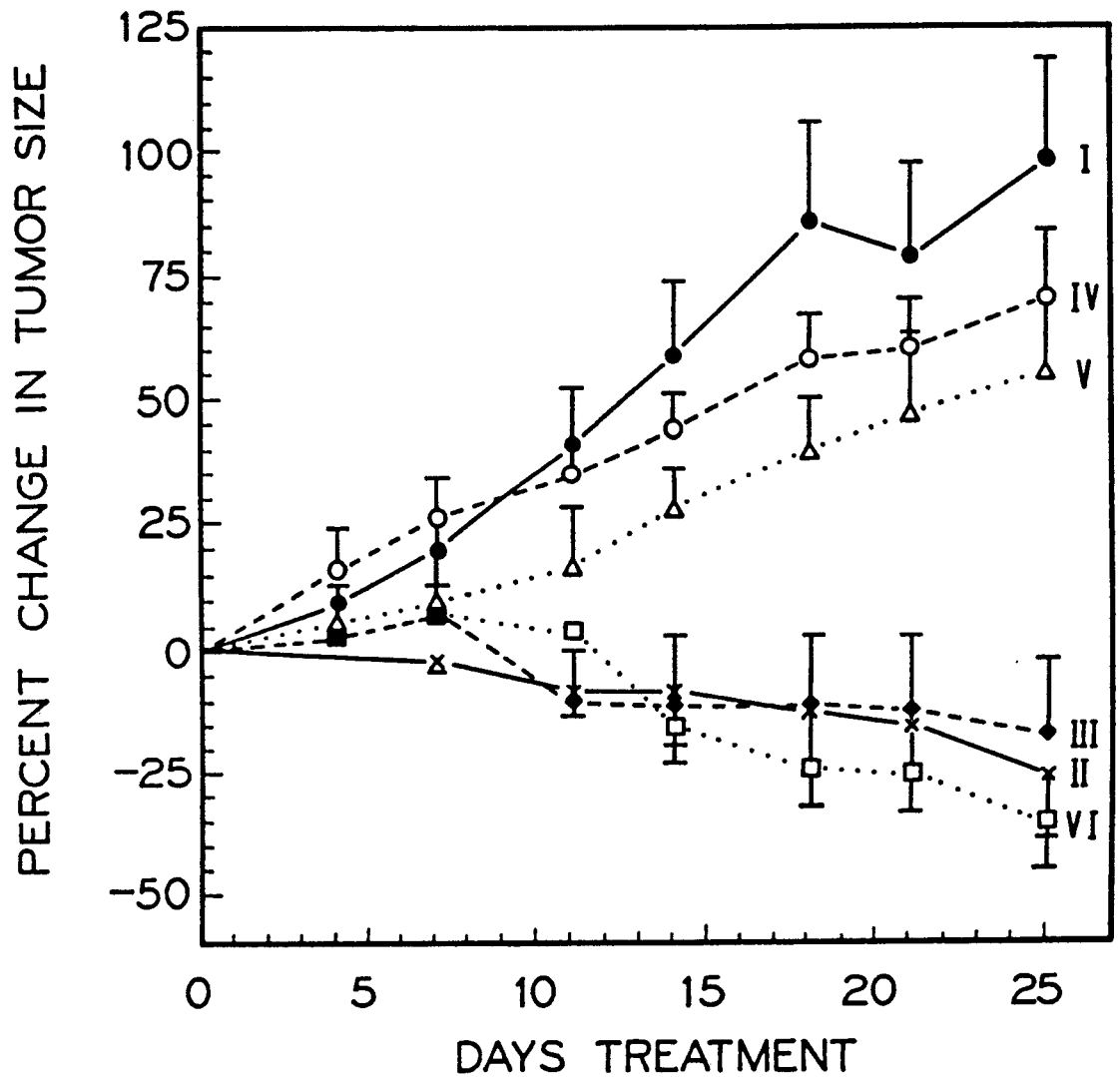
FIG. 5 is a graph showing the time-course change in volume of mammary tumors as a function of time (days) on the following diets, (group; dosage in mmol/kg diet; symbol): I, chow ( ); II, chow+2.0 mmol/kg HPR (X); III, chow+128 mmol/kg CGT ( ); IV, chow+0.75 mmol/kg HPR ( ); V, chow+64 mmol/kg CGT (Δ); VI, chow+0.75 mmol/kg HPR+64 mmol/kg CGT (□).

FIG. 5 is a graph showing the effect of the six diets on tumor growth. When tested separately (groups II and III), optimal doses of HPR (2 mmol/kg) or CGT (128 mmol/kg) decreased mammary tumor sizes by 15% and 25%, respectively. Tumors continued to grow in rats fed on the chow diets and on diets supplemented with low ineffective doses of calcium glucarate (group IV) or N-(4-hydroxyphenyl) retinamide (group V). At the low dose of HPR (0.75 mmol/kg) the size of the tumors increased by 70% compared to 98% in the controls. Similarly, at low dose CGT (64 mmol/kg) enhanced tumor growth, the size of the tumors increased by 55% over the 25 day period of observation. In contrast, the combination of CGT+HPR (group VI) had a marked synergistic inhibitory effect on rat mammary tumor growth over the 25 day period of observation. In this instance tumors decreased in size by 33% compared to the initial size at the beginning of the treatment.

The tumor measurements, being positively skewed, were log transformed in order to more accurately satisfy the assumptions of the analysis of variance. A repeated measures analysis of variance (with one between animal factor, treatment, and one repeat factor, time) was performed on the transformed data using baseline tumor size as a covariate. There was a statistically significant group by time interaction ($p<0.0001$) which indicates that the profile of tumor size over time depends upon group membership (See FIG. 5).

Upon employing follow-up Tukey multiple comparison tests (overall $\alpha=0.05$), adjusting for baseline tumor size, the following results were obtained. No statistically significant differences for the groups were discovered for the first three time periods (days 4, 7 and 11). At the fourth time period (day 14), groups II and III showed significantly decreased tumor sizes compared to the control group (group I). Also group III showed decreased tumor sizes compared to group IV. For the last three time periods (days 18, 21 and 25), groups I, III, and VI showed significantly decreased tumor sizes compared to the control group (group I), as well as to group IV and V. Although there is the potential for some error in measuring tumor size, the variability of the random error, i.e., the amount of error that could not be explained by group membership and days on treatment, was small, compared to the group difference at the latter time periods referred to above as being statistically significant.

It is known that weight gain/food intake may affect tumor growth as reported in Klurfeld et al., Determination of degree of energy restriction necessary to reduce DMBA-induced mammary tumorigenesis in rats during the promotion phase, J. Nutr. 119:286–291 (1989). Therefore, rats in all groups were weighed weekly and the results are shown in Table III below. Weight gain was essentially identical in all groups.

TABLE III

| Treatment | Average Weight of the Rats Just Before Treatment and at the End of Experiment | |
|---|---|---|
| | Initial Weight (gm) | Final Weight (gm) |
| Control (Chow + Vehicle) | 418 +/− 28 | 437 +/− 30 |
| HPR (2.0 mmol/kg) | 401 +/− 13 | 413 +/− 10 |
| CGT (4%) | 404 +/− 22 | 429 +/− 26 |
| HPR (0.75 mmol/kg) | 409 +/− 18 | 421 +/− 14 |
| CGT (2%) | 401 +/− 10 | 415 +/− 15 |
| HPR (0.75) + CGT (2%) | 418 +/− 15 | 428 +/− 18 |

The mechanism underlying the synergistic interaction of HPR and CGT is not clear. However, effective levels of glucarate are known to slightly reduce the level of circulating steroid hormones, including estrogen or testosterone (Walaszek et al., Carcinogenesis, 7, supra, possibly through phase II reactions, but it is questionable whether low levels act similarly. Effective doses of retinoid induces differentiation in some tumor cell histio-types, but again the effect at the lower dosages is unclear. To obtain some indication of mechanism, the estrogen receptor levels were measured in the tumors remaining in each group at the termination of the experiment. As shown in Table IV below, there is no significant difference in the estrogen/progesterone receptor profile in the group receiving the combination compared to the other groups.

TABLE IV

Effect of HPR and CGT on the Estrogen and Progesterone Receptors of the Established DMBA-Induced Mammary Tumors

| Treatment | N | Estrogen Receptors (Fmoles/mg Protein) | Progesterone Receptors (Fmoles/mg Protein) |
| --- | --- | --- | --- |
| Control (chow + vehicle) | 7 | 46.7 +/− 8.9 | 96.6 +/− 13.9 |
| HPR (2.0 mmol/kg) | 7 | 50.6 +/− 8.4 | 89.3 +/− 13.7 |
| CGT (4%) | 7 | 44.3 +/− 5.9 | 82.0 +/− 16.0 |
| HPR (0.75 mmol/kg) | 7 | 47.0 −/− 8.5 | 90.7 +/− 18.0 |
| CGT (2%) | 7 | 42.7 +/− 7.0 | 84.4 +/− 17.0 |
| HPR (0.75) + CGT (2%) | 7 | 51.7 +/− 9.0 | 96.3 +/− 29.0 |

When fed at low ineffective dosages, CGT and HPR had no observable inhibitory effect and indeed enhanced tumor development when fed separately. However, in combination they inhibited tumor growth by over 33% over a four week period. Furthermore, the combination caused tumor regression in greater than 80% of the rats, a very significant effect. These data are relevant where a drug is considered active in any particular tumor histio-type if it yields positive in at least 70% of the patients, Stolfi et al, Chemotherapeutic evaluation using clinical criteria in spontaneous autochthonous murine breat tumors, J. Natl. Cancer Inst. 80:52-55 (1988).

One possibility of the mechanism of action of the synergistic combination is that through conversion to D-glucaro-1,4-lactone and consequent inhibition of beta-glucuronidase, the net formation of HPR-glucuronide is enhanced. The D-glucaro-1,4-lactone compound is believed to be more effective and less toxic than the parent compound. Retinoid-glucuronides have previously been shown to have efficacy in tumor cell culture system, Zile et al., Induction of differentiation of human promyelocytic leukemia cell line HL-60 by retinoyl glucuronide, a biologically active metabolite of vitamin A, Proc. Natl. Acad, Sci. (U.S.A.) 84:2208-2212 (1987); Gallup et al., Effects of retinoid beta-glucuronides and N-retinoylamines on differentiation of HL-60 cells in vitro, Proc. Soc. Exp. Biol. Med. 186:269-294 (1987).

It is shown herein that combinations of low ineffective doses of HPR and CGT give a synergistic anti-tumor (chemotherapeutic) activity which is highly effective against rat mammary carcinoma.

It may be advantageous to formulate the compositions of the invention in unit dosage form for ease of administration and uniformity of dosage. A unit dosage formed, as used herein, refers to a physically discrete unit suitable for use as a unitary dosage for the mammalian subjects to be treated; each unit contains a predetermined quanitity of active material calculated to produce the desired therapeutic effect, in association with the required pharmaceutically acceptable carrier. Specifications for unit dosage forms are dictated by and directly dependent on (a) the unique characteristics of the active material in the particular therapeutic affect to be achieved, and (b) the limitations inherent in the art of compounding such an active material for the treatment of disease in living subjects having a diseased condition, without excessive cytotoxic effects.

Regression of breast cancer and inhibition of tumor growth may be obtained, for example, by the use of daily dosing for up to 50 to 100 days, or longer. Multiple dosing, or dosing on any desired periodic basis, may also be utilized. The therapeutically active ingredient is thus administered in an amount sufficient to aid regression and inhibition of further growth of the cancer, in the absence of excessive deleterious side-effects of a phyto-toxic nature.

The minimum dosage of the anticarcinogens used alone, consistent with maximum inhibition of carcinogenesis is approximately equivalent to 4 gm % CGT (4 gm/100 gm of chow diet) or 1.0-1.5 mmol/kg of HPR. This consideration is important since the human (in proportion to the surface area of the rodent) would need to consume approximately 40 gm of CGT per day while a dosage of 1.5 mmol/kg of retinoid would result in cummulative toxicity, with excess being deposited in the liver. Thus previous studies have been hindered by concern and actual problems with the toxicity of effective doses of the retinoids. The problems common to the use of these two classes of anticarcinogens when used separately, is circumvented by their combination. Furthermore, since their efficacy was tested using a carcinogenic protocol which utilized a single high dose of carcinogen (the minimum effective dose), it may be possible to reduce their concentrations even lower under chronic dose exposure to carcinogens. Thus, we have found that a combination of 2% CGT and 0.75 mmol/kg of retinoid is as effective as the single higher doses of each.

The anticarcinogenic combination of CGT and HPR compounds (active ingredients) of this invention can be administered to inhibit the formation of tumor cells or to decrease the risk of contracting cancer by any means that produces contact of the active ingredient with the agents site of action in the body of a human or animal. This anti-carcinogenic combination can also be administered to inhibit tumor growth and cause tumor regression. The combination can be administered by any conventional means available for use in conjunction with pharmaceuticals, either as individual therapeutic active ingredients or a combination of therapeutic active ingredients. The combination can be administered along, but is generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of receipient; nature and extent of symptoms, kind of concurrent treatment, frequency of treatment, and the effects desired. Usually a daily dosage of active ingredient can be about 5-400 mg/kg of body weight. Ordinarily, 10-300, and preferably 100-300 mg/kg body weight per day given in single doses or divided doses 2-4 times a day or in sustained release form is effect to obtain desired results. In a preferred embodiment the dietary supplement comprises approximately 0.01 to 0.02 parts by weight of the glucarolactone-based compounds for inhibiting beta-glucuronidase and approximately 0.0003 to 0.0006 parts by weight of the retinoid-based compound for elevating levels of cellular cAMP and of histone kinases.

Dosage forms (compositions) suitable for internal administration contain from about 1.0 mg to about 500 mg of active ingredient per unit. In these pharmaceutical compositions active ingredient will normally be present in an amount of 0.5-95%, by weight, based on the total weight of the composition.

The active ingredient can be administered in the diet or in solid dosage forms such as capsules, tablets and powders or in liquid dosage form, such as elixers, syrups and suspensions.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of the composition over a period of hours. Compressed tablets can be sugar-coated or film-coated to mask any unpleasant taste and protect the tablet from atmosphere, or enteric-coated for selective disintegration in the gastrointestinal tract.

Liquid dosage forms for oral administration can contain coloring and flavor to increase patient acceptance.

Useful pharmaceutical-dosage forms for administration of the compounds of this invention can be illustrated as follows:

CAPSULES: a large number of unit capsules are prepared by filling standard two-piece hard gelatin capsules each with 100 mg of powdered active ingredient, 175 mg of lactose, 24 mg of talc, and 6 mg magnesium stearate. A mixture of active ingredient in soybean oil is prepared and injected by means of a positive displacement pump into gelatin to form soft gelatin capsules containing 100 mg active ingredient. The capsules are washed and dried.

TABLETS: Large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of cornstarch and 98.8 mg of lactose. Appropriate coatings may be applied to increase pallatability or delayed absorption.

For treatment of non-human animals, the composition is preferably incorporated in animal feed, feed supplements or feed concentrates.

From the preceding, it can be seen that in accordance with the present invention, a novel composition comprising glucarolactone-based compounds and retinoid-based compounds is provided, the members of the compositions of which induce regression and/or inhibit the induction and growth of various malignant tumors in mammals.

It will be apparent that various changes may be made in the method of preparation and use, as well as in the particular substitution of therapeutically active compositions of the present invention. Accordingly, the preceding disclosure should be construed as illustrative only, and the scope of the claims should be incorporated in accordance with the claims appended hereto.

We claim:

1. A dietary supplement for use as a chemotherapeutic agent in treating mammary cancer in humans or animals via steady and prolonged inhibition of beta-glucuronidase and via elevation of the level of cellular cAMP (cyclic AMP) and of histone kinases, the supplement consisting essentially of approximately 0.01 to 0.02 parts by weight of calcium glucarate for inhibiting beta-glucuronidase and approximately 0.0003 to 0.0006 parts by weight of N-(4-hydroxyphenyl) retinamide for elevating levels of cellular cAMP and of histone kinases.

2. The dietary supplement of claim 1, wherein a daily dosage of the supplement is from about 100 to about 300 mg/kg body weight.

3. The dietary supplement of claim 1 wherein the supplement is administered promptly after the detection of the tumor.

4. A method of treating mammary cancer in humans or animals comprising administering an amount, which is safe and sufficient of the dietary supplement of claim 1 including the glucarolactone-based compound and the retinoid-based compound, or a pharmaceutically acceptable salt thereof to a patient having at least one mammary tumor.

5. The method of claim 4, wherein a daily dosage of the supplement is from about 100 to about 300 mg/kg body weight.

6. The method according to claim 4, wherein the supplement is administered promptly after the detection of the tumor.

7. A pharmaceutical composition for use as a chemotherapeutic agent for treating mammary cancer in humans or animals which comprises a therapeutically effective amount of the supplement of claim 1 in admixture with a pharmaceutically acceptable, substantially non-toxic carrier or excipient.

* * * * *